United States Patent
Wang et al.

(10) Patent No.: US 10,927,093 B1
(45) Date of Patent: Feb. 23, 2021

(54) METHOD FOR SYNTHESIZING 2-BENZYLIDENE TETRAHYDROTHIOPHENE DERIVATIVE

(71) Applicant: SOOCHOW UNIVERSITY, Suzhou (CN)

(72) Inventors: Shunyi Wang, Suzhou (CN); Shunjun Ji, Suzhou (CN); Jinghao Li, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 0 days.

(21) Appl. No.: 16/968,149

(22) PCT Filed: Feb. 26, 2018

(86) PCT No.: PCT/CN2018/077178
§ 371 (c)(1),
(2) Date: Aug. 6, 2020

(87) PCT Pub. No.: WO2019/153373
PCT Pub. Date: Aug. 15, 2019

(30) Foreign Application Priority Data

Feb. 9, 2018 (CN) .......................... 201810134894.1

(51) Int. Cl.
*C07D 333/08* (2006.01)
(52) U.S. Cl.
CPC .................................. *C07D 333/08* (2013.01)
(58) Field of Classification Search
CPC .................................................... C07D 333/08
See application file for complete search history.

(56) References Cited

PUBLICATIONS

Truce et al. J. Org. Chem. 1970, 35, 1834-1838 (Year: 1970).*

Ding et al, "Synthesis of 1,3-Dihydrobenzo[c]thiophene-imines via Tandem Reactions of o-(1-Alkynyl)benzamides and Lawesson's Reagent" Synthesis, 2012, 44, 920-926.

* cited by examiner

*Primary Examiner* — Matthew P Coughlin
(74) *Attorney, Agent, or Firm* — SZDC Law P.C.

(57) ABSTRACT

The present invention relates to a method for synthesizing a 2-benzylidene tetrahydrothiophene derivative, which comprises the step of reacting a (cyclopropylethynyl) aromatic cyclic compound of Formula (I) with a sulfur source in an organic solvent as a reaction medium in air atmosphere at 100-200° C. to obtain a 2-benzylidene tetrahydrothiophene derivative of Formula (III). The reaction route is as follows:

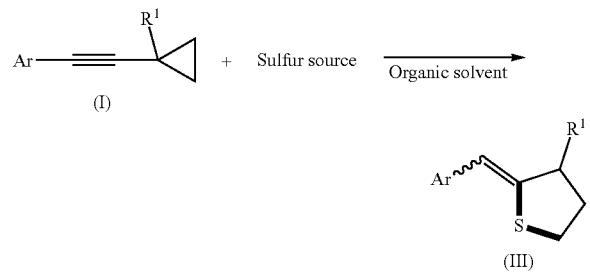

where Ar is selected from phenyl ring, a substituted phenyl ring, biphenylyl, thiophenyl ring or naphthyl ring, in which the substituent on the substituted phenyl ring is selected from the group consisting of halo, trifluoromethyl, cyano, a $C_1$-$C_{20}$ alkyl group and any combination thereof; and $R^1$ is selected from hydrogen or a $C_1$-$C_{20}$ alkyl group. The method of the present invention has the advantages of simple reaction conditions, convenient post-treatment, environmental friendliness, and requiring no transition metal catalysis.

11 Claims, No Drawings

METHOD FOR SYNTHESIZING 2-BENZYLIDENE TETRAHYDROTHIOPHENE DERIVATIVE

This application is the National Stage Application of PCT/CN2018/077178, filed on Feb. 26, 2018, which claims priority to Chinese Patent Application No. 201810134894.1, filed on Feb. 9, 2018, which is incorporated by reference for all purposes as if fully set forth herein.

FIELD OF THE INVENTION

The present invention relates to the technical field of organic synthesis, and particularly to a method for synthesizing a 2-benzylidene tetrahydrothiophene derivative.

DESCRIPTION OF THE RELATED ART

Natural or artificial organic sulfur-containing compounds play an important role in medicinal chemistry and biochemistry, and tetrahydrothiophene is particularly notable among many organic sulfur-containing compounds. In the past few decades, it has attracted the attention of many chemists, pharmacologists and biologists. The compound based on tetrahydrothiophene includes Biotin, a water-soluble vitamin that is involved in many biological functions and has been chemically synthesized on a large scale (*Org. Lett.*, 1999, 1:99-102). Representative biologically active tetrahydrothiophene derivatives include a 4'-thioadenine derivative that is a highly potent and highly selective A3 adenosine receptor antagonist (*Chem. Pharm. Bull.*, 1998, 46: 1339-1440), and 4'-thiocytidine that is an anti-HIV and HBV inhibitor (*J. Med. Chem*, 2007, 50: 3159-3162). Due to the excellent nucleophilic performance and coordination ability of sulfur atoms, the substituted tetrahydrothiophene compounds are often used as a ligand for transition metal catalysis, a nucleophilic organic small molecule catalyst, and a sulfur ylide precursor in organic synthesis. The 2-benzylidene tetrahydrothiophene derivative reported herein also has potential biological activity and catalytic ability, but the synthesis method therefor is rarely reported.

At present, the synthesis of 2-benzylidene tetrahydrothiophene is mainly achieved by generating sulfur radicals by a thiol having an unsaturated bond in the presence of a nickel catalyst or others to attack unsaturated bonds (*Tetrahedron Lett.*, 1998, 39, 8121-8124) or by preparing a special phosphorus ylide to undergo wittig reaction with a carbonyl group (*J. Org. Chem.*, 1979, 44 (16), 2911-2915). The reaction has the disadvantages of complex raw material preparation, expensive metal catalyst and others. Therefore, it is particularly important to explore the synthesis of a 2-benzylidene tetrahydrothiophene derivative with cheap and readily available raw materials in the absence of metal.

SUMMARY OF THE INVENTION

To solve the above technical problems, an object of the present invention is to provide a method for synthesizing a 2-benzylidene tetrahydrothiophene derivative. The method of the present invention has the advantages of simple reaction conditions, convenient post-treatment, environmental friendliness, and requiring no transition metal catalysis.

The present invention provides a method for synthesizing a 2-benzylidene tetrahydrothiophene derivative, which includes the step of reacting a (cyclopropylethynyl) aromatic cyclic compound of Formula (I) with a sulfur source in an organic solvent as a reaction medium in air atmosphere at 100-200° C. to obtain a 2-benzylidene tetrahydrothiophene derivative represented of Formula (III). The reaction route is as follows:

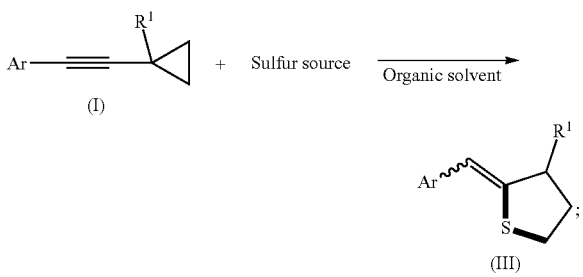

where Ar is selected from phenyl ring, a substituted phenyl ring, biphenylyl, thiophenyl ring or naphthyl ring, in which the substituent on the substituted phenyl ring is selected from the group consisting of halo, trifluoromethyl, cyano, a $C_1$-$C_{20}$ alkyl group and any combination thereof; and $R^1$ is selected from hydrogen or a $C_1$-$C_{20}$ alkyl group.

The wavy line in Formula (III) indicates that the product has different configurations and can be a mixture of cis-trans isomers, which contains both Z-configuration products and E-configuration products, or contains only Z-configuration products or E-configuration products.

Preferably, the alkyl group is a $C_1$-$C_5$ group. More preferably, the alkyl group is methyl.

More preferably, halo is chloro or bromo.

More preferably, Ar is a phenyl ring, and $R^1$ is hydrogen or methyl.

More preferably, Ar is selected from a substituted phenyl ring, biphenylyl, thiophenyl ring or naphthyl ring, in which the substituent on the substituted phenyl ring is selected from the group consisting of halo, trifluoromethyl, cyano, a $C_1$-$C_{20}$ alkyl group and any combination thereof; and $R^1$ is hydrogen. Preferably, the alkyl group is a $C_1$-$C_5$ group. More preferably, the alkyl group is methyl.

Preferably, the (cyclopropylethynyl) aromatic cyclic compound of Formula (I) is (cyclopropylethynyl)benzene (1), 1-chloro-4-(cyclopropylethynyl)benzene (2), 1-bromo-4-(cyclopropylethynyl)benzene (3), 1-(cyclopropylethynyl)-4-(trifluoro-methyl)benzene (4), 1-(cyclopropylethynyl)-4-methylbenzene (5), 4-(cyclopropyl-ethynyl)benzonitrile (6), 1-chloro-2-(cyclopropylethynyl)benzene (7), 1-(cyclopropyl-ethynyl)-2-methylbenzene (8), 1-(cyclopropylethynyl)-3-methyl-benzene (9), 1-chloro-3-(cyclopropylethynyl)benzene (10), 4-(cyclopropylethynyl)-1,1'-biphenyl(11), 1-(cyclopropylethynyl)naphthalene (12), 4-bromo-1-(cyclo-propyl-ethynyl)-2-methylbenzene (13), 2-chloro-4-(cyclopropylethynyl)-1-methylbenzene (14), 3-(cyclopropylethynyl)thiophene (15), or ((1-methylcyclopropyl)ethynyl)-benzene (16). The specific structural formulas of the compounds of Formula (I) corresponding to the above numbers are as follows:

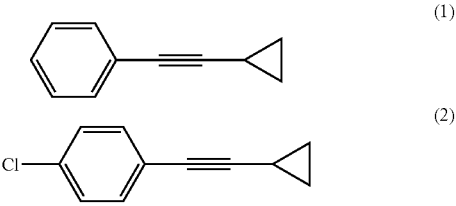

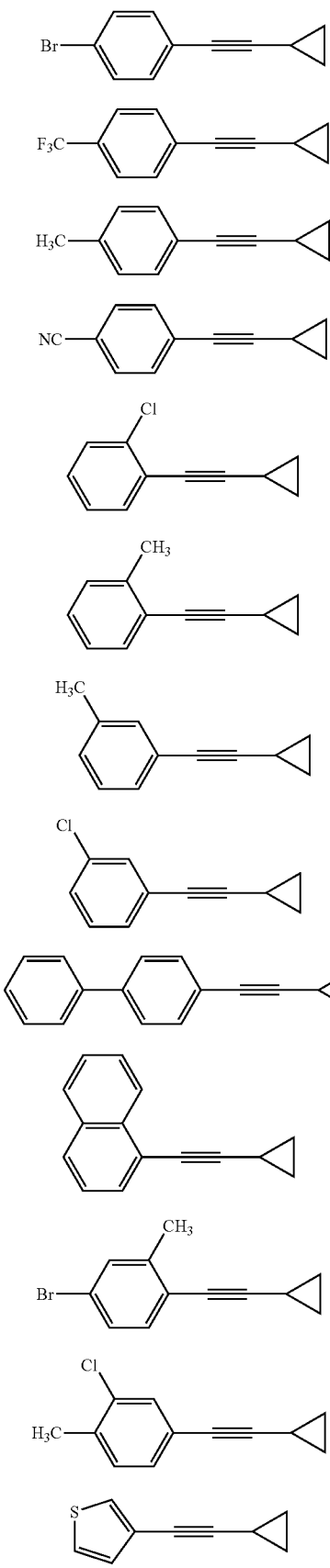

(3)
(4)
(5)
(6)
(7)
(8)
(9)
(10)
(11)
(12)
(13)
(14)
(15)

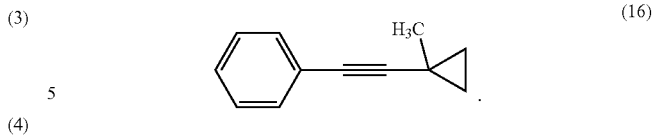

(16)

Preferably, the sulfur source is sodium sulfide and/or potassium sulfide. Sodium sulfide is sodium sulfide nonahydrate or anhydrous sodium sulfide, and potassium sulfide is anhydrous potassium sulfide or hydrated potassium sulfide. Preferably, the sulfur source is sodium sulfide nonahydrate ($Na_2S \cdot 9H_2O$).

Preferably, the molar ratio of the (cyclopropylethynyl) aromatic cyclic compound to the sulfur source is 1:1-6.

Preferably, the organic solvent is selected from the group consisting of N,N'-dimethyl formide (DMF), dimethyl sulfoxide (DMSO) N,N'-dimethyl acetamide (DMA) and any combination thereof. Preferably, the organic solvent is DMA.

Preferably, the ratio of the (cyclopropylethynyl) aromatic cyclic compound and the organic solvent in units of mole and milliliter, respectively is 0.3-1 mol:0.1-10 mL. Preferably, the ratio of the (cyclopropylethynyl) aromatic cyclic compound to the organic solvent is 0.3-1 mol:0.5-3 mL. More preferably, the ratio of the (cyclopropylethynyl) aromatic cyclic compound to the organic solvent is 0.5 mol:2.5 mL.

Preferably, the reaction time is 8-20 h. Preferably, the reaction time is 9-11 hrs.

Preferably, the reaction temperature is 130-150° C. More preferably, the reaction temperature is 150° C.

More preferably, the above synthesis method further comprises column chromatography after the reaction is completed to obtain the compound of Formula (III).

For example, if DMA is used as a solvent, the reaction principle underlying the reaction involving (cyclopropylethynyl)benzene (1a in the scheme shown below) and sodium sulfide nonahydrate (2 in the scheme shown below) is as follows:

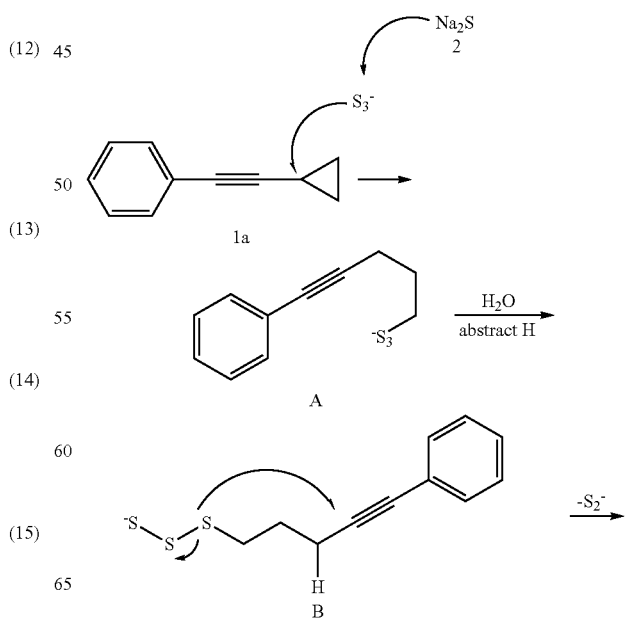

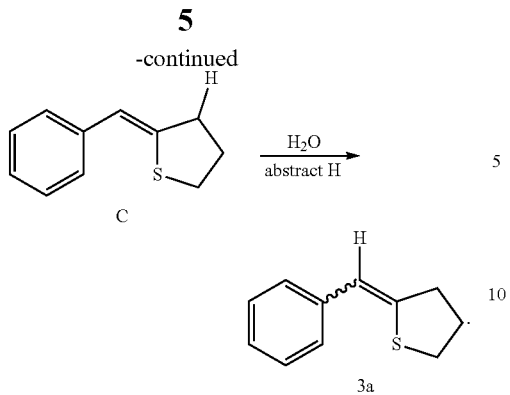

In the scheme, sodium sulfide nonahydrate 2 produces negatively charged trisulfur radicals ($S_3^-$.) in situ in the solvent DMA. Then the negatively charged trisulfur radicals attack and open the three-membered ring in (cyclopropylethynyl) benzene 1a, to produce an intermediate A having a carbon free radical at the propargylic position and a negatively charged trisulfur group. The carbon radical abstracts hydrogen in water to produce an intermediate B. Then the negatively charged trisulfur group undergoes homolysis of sulfur-sulfur bond, and the generated new sulfur radical is added to the carbon-carbon triple bond in the alkyne to produce an intermediate C. Then, the alkenyl radical abstracts hydrogen in water to produce the product 3a that is 2-benzylidene tetrahydrothiophene. The water mentioned above comes from the crystal water in the sulfur source or the trace water contained in the organic solvent. The other (cyclopropylethynyl) aromatic cyclic compounds involved in the present invention participate in the reaction through a similar mechanism.

By virtue of the above solution, the present invention has at least the following advantages.

In the present invention, a (cyclopropylethynyl) aromatic cylic compound is used as a reaction raw material, cheap, readily available, easy-to-operate, and low-toxic sodium sulfide or potassium sulfate is directly used as a sulfur source, and DMA is used as a solvent to prepare a 2-benzylidene tetrahydrothiophene compound without metal catalysis.

Compared with the prior art, the present invention provides a green, simple and efficient method for synthesizing a 2-benzylidene tetrahydrothiophene compound. The method has the advantages of cheap and readily available raw materials, simple reaction conditions, convenient post-treatment, requiring no metal catalysis, high atom economy, and high yield, thus meeting the requirements of green chemistry. The experimental results show that the method provided in the present invention can be used to synthesize 2-benzylidene tetrahydrothiophene compounds with a yield of 36%-76%.

The above description is only an overview of the technical solutions of the present invention. In order to illustrate the technical means of the present invention more clearly and implement the technical solutions in accordance with the specification, the preferred embodiments of the invention are described hereinafter in more detail.

DETAILED DESCRIPTION OF THE PREFERRED EMBODIMENTS

The invention will be described in further detail with reference to embodiments. The following examples are intended to illustrate the present invention, instead of limit the scope of the present invention.

In the following examples of the present invention, the specific structural formula of the (cyclopropylethynyl) aromatic cyclic compound corresponding to each number above is as follows:

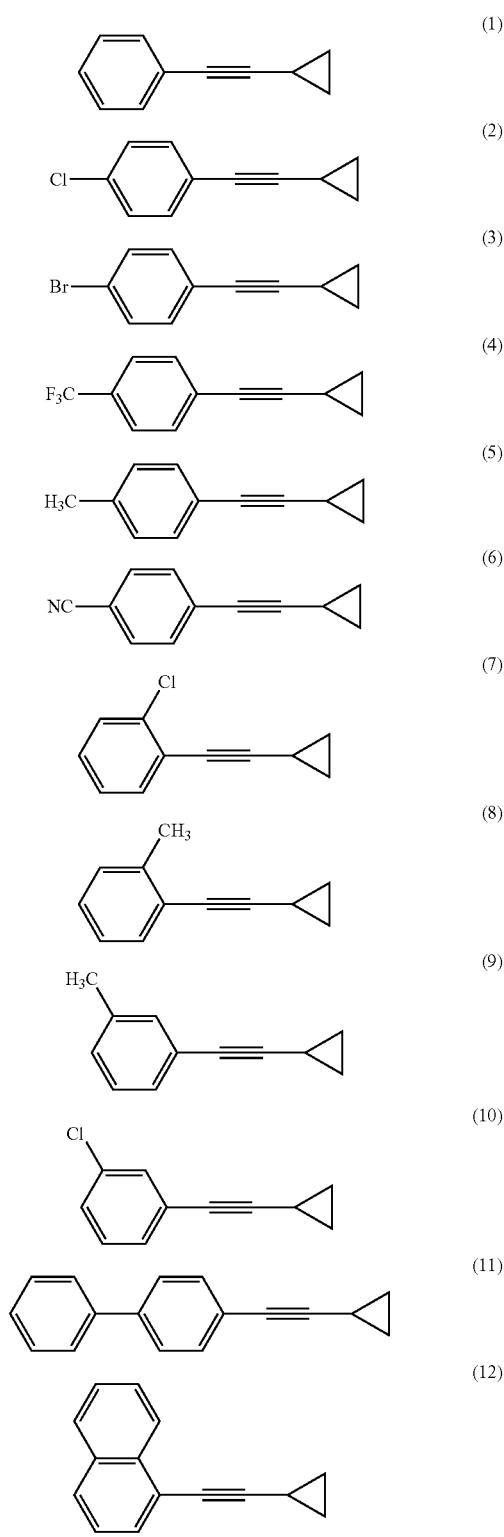

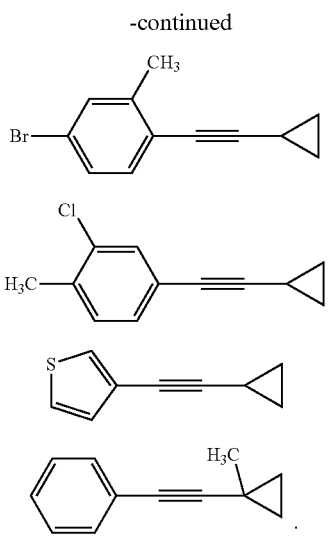

Example 1

Synthesis of 2-benzylidene tetrahydrothiophene (Cyclopropylethynyl)benzene (compound corresponding to No. (1), 0.0711 g, 0.5 mmol) and sodium sulfide nonahydrate (0.2402 g, 1.0 mmol) were weighed and fed to a 25 mL reaction tube. DMA (2.5 mL) was added as a solvent, and the reaction was performed under stirring for 9 hrs at 150° C. After the reaction, the reaction solution was extracted with ethyl acetate and saturated brine, dried over anhydrous sodium sulfate and filtered with suction. The resulting filtrate was rotary evaporated to dryness, the sample was loaded, and separated by column chromatography (conditions: stationary phase 300-400-mesh silica gel powder, and mobile phase petroleum ether) to afford a reaction product (0.0608 g).

The reaction product was characterized. The results are shown below:

$^1$H NMR (400 MHz, CDCl$_3$) δ=7.42 (d, J=7.3 Hz, 1H), 7.35-7.24 (m, 2H), 7.24-7.10 (m, 1H), 6.46 (s, 0.76×1H), 6.42 (t, J=1.9 Hz, 0.24×1H), 3.14 (t, J=6.4 Hz, 0.76×2H), 3.03 (t, J=6.4 Hz, 0.24×2H), 2.84-2.74 (m, 2H), 2.12-2.05 (m, 0.24×2H), 1.98 (p, J=6.6 Hz, 0.76×2H); $^{13}$C NMR (100 MHz, CDCl$_3$) δ=145.6, 143.2, 138.4, 137.8, 128.3, 127.7, 127.7, 125.7, 125.7, 117.3, 117.1, 40.3, 35.7, 34.4, 33.0, 31.1, 28.4 ppm.

According to the characterization data, the prepared product is 2-benzylidene tetrahydrothiophene (E/Z=24:76) (purity >95%); and the yield of the product is calculated to be 69%.

Example 2

Synthesis of 2-(4-chlorobenzylidene)tetrahydrothiophene 1-chloro-4-(cyclopropylethynyl)benzene (compound corresponding to No. (2), 0.0883 g, 0.5 mmol) and sodium sulfide nonahydrate (0.2402 g, 1.0 mmol) were weighed and fed to a 25 mL reaction tube. DMA (2.5 mL) was added as a solvent, and the reaction was performed under stirring for 12 hrs at 150° C. After the reaction, the reaction solution was extracted with ethyl acetate and saturated brine, dried over anhydrous sodium sulfate and filtered with suction. The resulting filtrate was rotary evaporated to dryness, the sample was loaded, and separated by column chromatography (conditions: stationary phase 300-400-mesh silica gel powder, and mobile phase petroleum ether) to afford a reaction product (0.0759 g).

The reaction product was characterized. The results are shown below:

$^1$H NMR (400 MHz, CDCl$_3$) δ=7.40-7.31 (m, 2H), 7.31-7.25 (m, 2H), 6.41 (s, 0.95×1H), 6.36 (s, 0.05×1H), 3.19 (t, J=6.4 Hz, 0.95×2H), 3.07 (t, J=6.4 Hz, 0.05×2H), 2.80 (td, J=6.8, 1.5 Hz, 2H), 2.13 (p, J=6.6 Hz, 0.05×2H), 2.02 (p, J=6.6 Hz, 0.95×2H); $^{13}$C NMR (100 MHz, CDCl$_3$) δ=144.3, 136.4, 131.1, 128.9, 128.5, 115.9, 40.4, 35.8, 28.5 ppm.

According to the characterization data, the prepared product is pure 2-(4-chlorobenzylidene) tetrahydrothiophene (E/Z=5:95) (purity >95%); and the yield of the product is calculated to be 72%.

Example 3

Synthesis of 2-(4-bromobenzylidene)tetrahydrothiophene 1-bromo-4-(cyclopropylethynyl)benzene (compound corresponding to No. (3), 0.1105 g, 0.5 mmol) and sodium sulfide nonahydrate (0.2402 g, 1.0 mmol) were weighed and fed to a 25 mL reaction tube. DMA (2.5 mL) was added as a solvent, and the reaction was performed under stirring for 12 hrs at 150° C. After the reaction, the reaction solution was extracted with ethyl acetate and saturated brine, dried over anhydrous sodium sulfate and filtered with suction. The resulting filtrate was rotary evaporated to dryness, the sample was loaded, and separated by column chromatography (conditions: stationary phase 300-400-mesh silica gel powder, and mobile phase petroleum ether) to afford a reaction product (0.0842 g).

The reaction product was characterized. The results are shown below:

$^1$H NMR (400 MHz, CDCl$_3$) δ=7.48-7.38 (m), 7.32-7.27 (m), 7.12-7.04 (m), 6.41 (s, 0.77×1H), 6.36 (t, J=2.0 Hz, 0.23×1H), 3.20 (t, J=6.4 Hz, 0.77×2H), 3.09 (t, J=6.4 Hz, 0.23×2H), 2.87-2.76 (m, 2H), 2.15 (p, J=6.6 Hz, 0.23×2H), 2.05 (p, J=6.6 Hz, 0.77×2H); $^{13}$C NMR (100 MHz, CDCl$_3$) δ=146.8, 144.5, 137.3, 136.8, 131.4, 131.4, 129.3, 129.2, 119.3, 119.2, 116.1, 116.0, 40.4, 35.9, 34.5, 33.1, 31.1, 28.5 ppm.

According to the characterization data, the prepared product is pure 2-(4-bromobenzylidene) tetrahydrothiophene (E/Z=23:77) (purity >95%); and the yield of the product is calculated to be 66%.

Example 4

Synthesis of 2-(4-(trifluoromethyl)benzylidene)tetrahydrothiophene 1-(cyclopropylethynyl)-4-(trifluoromethyl)benzene (compound corresponding to No. (4), 0.1051 g, 0.5 mmol) and sodium sulfide nonahydrate (0.2402 g, 1.0 mmol) were weighed and fed to a 25 mL reaction tube. DMA (2.5 mL) was added as a solvent, and the reaction was performed under stirring for 12 hrs at 150° C. After the reaction, the reaction solution was extracted with ethyl acetate and saturated brine, dried over anhydrous sodium sulfate and filtered with suction. The resulting filtrate was rotary evaporated to dryness, the sample was loaded, and separated by column chromatography (conditions: stationary phase 300-400-mesh silica gel powder, and mobile phase petroleum ether) to afford a reaction product (0.0831 g).

The reaction product was characterized. The results are shown below:

$^1$H NMR (400 MHz, CDCl$_3$) δ=7.62-7.46 (m), 7.28 (d, J=8.2 Hz), 6.49 (s, 0.7×1H), 6.44 (s, 0.3×1H), 3.21 (t, J=6.4 Hz, 0.7×2H), 3.08 (t, J=6.4 Hz, 0.3×2H), 2.91-2.76 (m, 2H), 2.15 (p, J=6.6 Hz, 0.3×2H), 2.04 (p, J=6.6 Hz, 0.7×2H); $^{13}$C NMR (100 MHz, CDCl$_3$) δ=149.2, 147.0, 141.8 (d, J=1.3 Hz), 141.4, 129.5, 129.2, 128.6, 127.7, 127.7, 127.5, 127.2 (d, J=32.1 Hz), 127.1, 126.8, 125.3 (q, J=7.5 Hz), 124.5 (d, J=270 Hz), 120.5, 115.9, 115.8, 40.6, 36.0, 34.7, 33.1, 31.2, 28.4 ppm.

According to the characterization data, the prepared product is pure 2-(4-(trifluoromethyl)benzylidene) tetrahydrothiophene (E/Z=30:70) (purity >95%); and the yield of the product is calculated to be 68%.

Example 5

Synthesis of 2-(4-methylbenzylidene)tetrahydrothiophene 1-(cyclopropylethynyl)-4-methylbenzene (compound corresponding to No. (5), 0.0781 g, 0.5 mmol) and sodium sulfide nonahydrate (0.2402 g, 1.0 mmol) were weighed and fed to a 25 mL reaction tube. DMA (2.5 mL) was added as a solvent, and the reaction was performed under stirring for 12 hrs at 150° C. After the reaction, the reaction solution was extracted with ethyl acetate and saturated brine, dried over anhydrous sodium sulfate and filtered with suction. The resulting filtrate was rotary evaporated to dryness, the sample was loaded, and separated by column chromatography (conditions: stationary phase 300-400-mesh silica gel powder, and mobile phase petroleum ether) to afford a reaction product (0.0495 g).

The reaction product was characterized. The results are shown below:

$^1$H NMR (400 MHz, CDCl$_3$) δ=7.35 (d, J=8.1 Hz), 7.20-7.12 (m), 6.48 (s, 0.87×1H), 6.43 (t, J=2.0 Hz, 0.13×1H), 3.20 (t, J=6.4 Hz, 0.87×2H), 3.09 (t, J=6.4 Hz, 0.13×2H), 2.83 (td, J=6.8, 1.5 Hz, 2H), 2.35 (s, 2H), 2.15 (p, J=6.6 Hz, 0.13×2H), 2.05 (p, J=6.6 Hz, 0.87×2H); $^{13}$C NMR (100 MHz, CDCl$_3$) δ=144.4, 142.0, 135.7, 135.4, 135.3, 135.1, 129.1, 127.66, 127.6, 117.2, 117.0, 40.2, 35.6, 34.3, 32.9, 31.1, 28.5, 21.3, 21.2 ppm.

According to the characterization data, the prepared product is pure 2-(4-methylbenzylidene) tetrahydrothiophene (E/Z=13:87) (purity >95%); and the yield of the product is calculated to be 52%.

Example 6

Synthesis of (Z)-4-((dihydrothiophen-2(3H)-ylidene)methyl)benzamide 4-(cyclopropylethynyl)benzonitrile (compound corresponding to No. (6), 0.0836 g, 0.5 mmol) and sodium sulfide nonahydrate (0.2402 g, 1.0 mmol) were weighed and fed to a 25 mL reaction tube. DMA (2.5 mL) was added as a solvent, and the reaction was performed under stirring for 12 hrs at 150° C. After the reaction, the reaction solution was extracted with ethyl acetate and saturated brine, dried over anhydrous sodium sulfate and filtered with suction. The resulting filtrate was rotary evaporated to dryness, the sample was loaded, and separated by column chromatography (conditions: stationary phase 300-400-mesh silica gel powder, and mobile phase petroleum ether) to afford a reaction product (0.0526 g).

The reaction product was characterized. The results are shown below:

$^1$H NMR (400 MHz, DMSO-d$_6$) δ=8.07-7.68 (m, 3H), 7.52-7.14 (m, 3H), 6.55 (s, 1H), 3.19 (s, 2H), 2.80 (s, 2H), 1.94 (s, 2H); $^{13}$C NMR (100 MHz, DMSO) δ=167.6, 146.3, 140.3, 131.0, 127.7, 126.7, 115.7, 40.0, 35.4, 28.0 ppm.

According to the characterization data, the prepared product is pure (Z)-4-((dihydrothiophen-2(3H)-ylidene)methyl)benzamide (purity >95%); and the yield of the product is calculated to be 48%.

Example 7

Synthesis of (Z)-2-(2-chlorobenzylidene)tetrahydrothiophene 1-chloro-2-(cyclopropylethynyl)benzene (compound corresponding to No. (7), 0.0883 g, 0.5 mmol) and sodium sulfide nonahydrate (0.2402 g, 1.0 mmol) were weighed and fed to a 25 mL reaction tube. DMA (2.5 mL) was added as a solvent, and the reaction was performed under stirring for 12 hrs at 150° C. After the reaction, the reaction solution was extracted with ethyl acetate and saturated brine, dried over anhydrous sodium sulfate and filtered with suction. The resulting filtrate was rotary evaporated to dryness, the sample was loaded, and separated by column chromatography (conditions: stationary phase 300-400-mesh silica gel powder, and mobile phase petroleum ether) to afford a reaction product (0.0579 g).

The reaction product was characterized. The results are shown below:

$^1$H NMR (400 MHz, CDCl$_3$) δ=7.73 (dd, J=7.8, 1.4 Hz, 1H), 7.35 (dd, J=8.0, 1.2 Hz, 1H), 7.29-7.23 (m, 1H), 7.09 (td, J=7.7, 1.5 Hz, 1H), 6.76 (s, 1H), 3.18 (t, J=6.4 Hz, 2H), 2.87 (td, J=6.9, 1.6 Hz, 2H), 2.06 (p, J=6.6 Hz, 2H); $^{13}$C NMR (100 MHz, CDCl$_3$) δ=146.3, 135.8, 132.8, 129.5, 128.4, 127.0, 126.6, 113.3, 40.3, 35.4, 28.5 ppm.

According to the characterization data, the prepared product is pure (Z)-2-(2-chlorobenzylidene) tetrahydrothiophene (purity >95%); and the yield of the product is calculated to be 55%.

Example 8

Synthesis of 2-(2-methylbenzylidene)tetrahydrothiophene 1-(cyclopropylethynyl)-2-methylbenzene (compound corresponding to No. (8), 0.0781 g, 0.5 mmol) and sodium sulfide nonahydrate (0.2402 g, 1.0 mmol) were weighed and fed to a 25 mL reaction tube. DMA (2.5 mL) was added as a solvent, and the reaction was performed under stirring for 12 hrs at 150° C. After the reaction, the reaction solution was extracted with ethyl acetate and saturated brine, dried over anhydrous sodium sulfate and filtered with suction. The resulting filtrate was rotary evaporated to dryness, the sample was loaded, and separated by column chromatography (conditions: stationary phase 300-400-mesh silica gel powder, and mobile phase petroleum ether) to afford a reaction product (0.0647 g).

The reaction product was characterized. The results are shown below:

$^1$H NMR (400 MHz, CDCl$_3$) δ=7.59 (d, J=7.7 Hz), 7.26-7.01 (m), 6.52 (s, 0.82×1H), 6.44 (s, 0.18×1H), 3.09 (t,

J=6.4 Hz, 0.82×2H), 3.05 (t, J=6.4 Hz, 0.18×2H), 2.79 (td, J=6.8, 1.6 Hz, 0.82×2H), 2.69 (td, J=6.8, 2.1 Hz, 0.18×2H), 2.28 (s, 0.82×3H), 2.25 (s, 0.18×3H), 2.02 (dp, J=19.9, 6.6 Hz, 2H); $^{13}$C NMR (100 MHz, CDCl$_3$) δ=145.2, 144.0, 137.5, 136.8, 135.7, 135.5, 123.0, 129.9, 128.1, 127.1, 126.2, 125.7, 125.6, 115.7, 114.6, 39.8, 34.9, 34.3, 33.1, 30.7, 28.6, 20.1 ppm.

According to the characterization data, the prepared product is pure 2-(2-methylbenzylidene) tetrahydrothiophene (E/Z=18:82) (purity >95%); and the yield of the product is calculated to be 68%.

Example 9

Synthesis of 2-(3-methylbenzylidene)tetrahydrothiophene 1-(cyclopropylethynyl)-3-methylbenzene (compound corresponding to No. (9), 0.0781 g, 0.5 mmol) and sodium sulfide nonahydrate (0.2402 g, 1.0 mmol) were weighed and fed to a 25 mL reaction tube. DMA (2.5 mL) was added as a solvent, and the reaction was performed under stirring for 12 hrs at 150° C. After the reaction, the reaction solution was extracted with ethyl acetate and saturated brine, dried over anhydrous sodium sulfate and filtered with suction. The resulting filtrate was rotary evaporated to dryness, the sample was loaded, and separated by column chromatography (conditions: stationary phase 300-400-mesh silica gel powder, and mobile phase petroleum ether) to afford a reaction product (0.0647 g).

The reaction product was characterized. The results are shown below:

$^{1}$H NMR (400 MHz, CDCl$_3$) δ=7.30-7.11 (m), 6.98 (dd, J=23.7, 7.3 Hz), 6.42 (s, 0.83×1H), 6.38 (s, 0.17×1H), 3.13 (t, J=6.4 Hz, 0.83×2H), 3.01 (t, J=6.4 Hz, 0.17×2H), 2.78 (dtd, J=8.4, 6.9, 1.8 Hz, 2H), 2.32 (d, J=9.5 Hz, 3H), 2.11-2.03 (m, 0.17×2H), 1.97 (p, J=6.6 Hz, 0.83×2H); $^{13}$C NMR (100 MHz, CDCl$_3$) δ=145.3, 142.9, 137.7, 137.7, 123.0, 128.5, 128.4, 128.3, 128.2, 127.4, 126.5, 126.4, 126.2, 124.7, 117.2, 117.1, 40.2, 35.6, 34.3, 32.8, 31.1, 28.4, 21.6, 21.4 ppm.

According to the characterization data, the prepared product is pure 2-(3-methylbenzylidene) tetrahydrothiophene (E/Z=17:83) (purity >95%); and the yield of the product is calculated to be 68%.

Example 10

Synthesis of 2-(3-chlorobenzylidene)tetrahydrothiophene 1-chloro-3-(cyclopropylethynyl)benzene (compound corresponding to No. (10), 0.0883 g, 0.5 mmol) and sodium sulfide nonahydrate (0.2402 g, 1.0 mmol) were weighed and fed to a 25 mL reaction tube. DMA (2.5 mL) was added as a solvent, and the reaction was performed under stirring for 12 hrs at 150° C. After the reaction, the reaction solution was extracted with ethyl acetate and saturated brine, dried over anhydrous sodium sulfate and filtered with suction. The resulting filtrate was rotary evaporated to dryness, the sample was loaded, and separated by column chromatography (conditions: stationary phase 300-400-mesh silica gel powder, and mobile phase petroleum ether) to afford a reaction product (0.0769 g).

The reaction product was characterized. The results are shown below:

$^{1}$H NMR (400 MHz, CDCl$_3$) δ=7.40 (d, J=1.6 Hz, 1H), 7.25 (dq, J=13.8, 7.9 Hz, 2H), 7.12 (d, J=7.8 Hz, 1H), 6.41 (s, 0.92×1H), 6.36 (s, 0.08×1H), 3.20 (t, J=6.4 Hz, 0.92×2H), 3.08 (t, J=6.4 Hz, 0.08×2H), 2.83 (td, J=6.8, 1.4 Hz, 2H), 2.09 (dp, J=19.9, 6.6 Hz, 2H); $^{13}$C NMR (100 MHz, CDCl$_3$) δ=145.4, 139.7, 134.3, 129.6, 127.6, 125.7, 125.7, 115.8, 40.5, 35.9, 28.5 ppm.

According to the characterization data, the prepared product is pure 2-(3-chlorobenzylidene) tetrahydrothiophene (E/Z=8:92) (purity >95%); and the yield of the product is calculated to be 73%.

Example 11

2-([1,1'-biphenyl]-4-ylmethylidene)tetrahydrothiophene 4-(cyclopropylethynyl)-1,1'-biphenyl (compound corresponding to No. (11), 0.1091 g, 0.5 mmol) and sodium sulfide nonahydrate (0.2402 g, 1.0 mmol) were weighed and fed to a 25 mL reaction tube. DMA (2.5 mL) was added as a solvent, and the reaction was performed under stirring for 12 hrs at 150° C. After the reaction, the reaction solution was extracted with ethyl acetate and saturated brine, dried over anhydrous sodium sulfate and filtered with suction. The resulting filtrate was rotary evaporated to dryness, the sample was loaded, and separated by column chromatography (conditions: stationary phase 300-400-mesh silica gel powder, and mobile phase petroleum ether) to afford a reaction product (0.0959 g).

The reaction product was characterized. The results are shown below:

$^{1}$H NMR (400 MHz, CDCl$_3$) δ=7.56 (ddd, J=25.3, 12.8, 4.8 Hz, 6H), 7.42 (t, J=7.7 Hz, 2H), 7.36-7.27 (m, 1H), 6.52 (s, 0.85×1H), 6.47 (s, 0.15×1H), 3.22 (t, J=6.4 Hz, 0.85×2H), 3.10 (t, J=6.4 Hz, 0.15×2H), 2.87 (dtd, J=8.2, 6.9, 1.8 Hz, 2H), 2.17 (p, J=6.6 Hz, 0.15×2H), 2.06 (p, J=6.6 Hz, 0.85×2H); $^{13}$C NMR (100 MHz, CDCl$_3$) δ=145.9, 143.6, 141.0, 140.8, 138.3, 137.5, 137.0, 128.8, 128.1, 127.2, 127.1, 127.0, 127.0, 116.9, 116.7, 40.4, 35.8, 34.5, 33.0, 31.2, 28.5 ppm.

According to the characterization data, the prepared product is pure 2-([1,1'-biphenyl]-4-ylmethylidene)tetrahydrothiophene (E/Z=15:85) (purity >95%); and the yield of the product is calculated to be 76%.

Example 12

Synthesis of 2-(naphthalen-1-ylmethylidene)tetrahydrothiophene 1-(cyclopropylethynyl)naphthalene (compound corresponding to No. (12), 0.0961 g, 0.5 mmol) and sodium sulfide nonahydrate (0.2402 g, 1.0 mmol) were weighed and fed to a 25 mL reaction tube. DMA (2.5 mL) was added as a solvent, and the reaction was performed under stirring for 12 hrs at 150° C. After the reaction, the reaction solution was extracted with ethyl acetate and saturated brine, dried over anhydrous sodium sulfate and filtered with suction. The resulting filtrate was rotary evaporated to dryness, the sample was loaded, and separated by column chromatography (conditions: stationary phase 300-400-mesh silica gel powder, and mobile phase petroleum ether) to afford a reaction product (0.0679 g).

The reaction product was characterized. The results are shown below:

¹H NMR (400 MHz, CDCl₃) δ=7.98-7.87 (m, 1H), 7.71-7.60 (m, 2H), 7.55 (d, J=8.2 Hz, 1H), 7.31 (dddd, J=14.0, 12.3, 7.2, 5.4 Hz, 3H), 6.91 (s, 0.76×1H), 6.81 (s, 0.24×1H), 2.92 (t, J=6.4 Hz, 2H), 2.70 (td, J=6.9, 1.6 Hz, 0.76×2H), 2.51 (td, J=6.8, 2.1 Hz, 0.24×2H), 1.91-1.77 (m, 2H); ¹³C NMR (100 MHz, CDCl₃) δ=146.9, 145.9, 135.6, 135.0, 133.7, 133.6, 131.6, 131.3, 128.5, 128.4, 126.7, 126.6, 125.8, 125.8, 125.7, 125.6, 125.6, 125.5, 125.3, 125.2, 124.7, 124.0, 114.4, 113.4, 39.6, 34.7, 34.6, 33.3, 30.5, 28.6 ppm.

According to the characterization data, the prepared product is pure 2-(naphthalen-1-ylmethylidene) tetrahydrothiophene (E/Z=24:76) (purity >95%); and the yield of the product is calculated to be 60%.

Example 13

Synthesis of 2-(4-bromo-2-methylbenzylidene)tetrahydrothiophene 4-bromo-1-(cyclopropylethynyl)-2-methylbenzene (compound corresponding to No. (13), 0.1176 g, 0.5 mmol) and sodium sulfide nonahydrate (0.2402 g, 1.0 mmol) were weighed and fed to a 25 mL reaction tube. DMA (2.5 mL) was added as a solvent, and the reaction was performed under stirring for 12 hrs at 150° C. After the reaction, the reaction solution was extracted with ethyl acetate and saturated brine, dried over anhydrous sodium sulfate and filtered with suction. The resulting filtrate was rotary evaporated to dryness, the sample was loaded, and separated by column chromatography (conditions: stationary phase 300-400-mesh silica gel powder, and mobile phase petroleum ether) to afford a reaction product (0.0875 g).

The reaction product was characterized. The results are shown below:

¹H NMR (400 MHz, CDCl₃) δ=7.45 (d, J=8.3 Hz), 7.37-7.15 (m, 2H), 7.01 (d, J=8.1 Hz), 6.41 (s, 0.79×1H), 6.32 (s, 0.21×1H), 3.11 (t, J=6.4 Hz, 0.79×2H), 3.06 (t, J=6.4 Hz, 0.21×2H), 2.78 (td, J=6.8, 1.6 Hz, 0.79×2H), 2.64 (td, J=6.8, 2.1 Hz, 0.21×2H), 2.22 (d, J=9.9 Hz, 3H), 2.12-1.93 (m, 2H); ¹³C NMR (100 MHz, CDCl₃) δ=146.4, 145.1, 137.9, 137.7, 136.4, 135.8, 132.6, 132.6, 129.5, 128.7, 128.6, 128.5, 119.5, 119.4, 114.4, 113.5, 39.9, 35.1 34.3, 33.2, 30.7, 28.6, 19.9, 19.9 ppm.

According to the characterization data, the prepared product is pure 2-(4-bromo-methylbenzylidene) tetrahydrothiophene (E/Z=21:79) (purity >95%); and the yield of the product is calculated to be 65%.

Example 14

Synthesis of 2-(3-chloro-4-methylbenzylidene)tetrahydrothiophene 2-chloro-4-(cyclopropylethynyl)-1-methylbenzene (compound corresponding to No. (14), 0.0953 g, 0.5 mmol) and sodium sulfide nonahydrate (0.2402 g, 1.0 mmol) were weighed and fed to a 25 mL reaction tube. DMA (2.5 mL) was added as a solvent, and the reaction was performed under stirring for 12 hrs at 150° C. After the reaction, the reaction solution was extracted with ethyl acetate and saturated brine, dried over anhydrous sodium sulfate and filtered with suction. The resulting filtrate was rotary evaporated to dryness, the sample was loaded, and separated by column chromatography (conditions: stationary phase 300-400-mesh silica gel powder, and mobile phase petroleum ether) to afford a reaction product (0.0641 g).

The reaction product was characterized. The results are shown below:

¹H NMR (400 MHz, CDCl₃) δ=7.39 (d, J=1.6 Hz), 7.24-7.08 (m, 2H), 6.96 (dd, J=7.9, 1.6 Hz), 6.35 (s, 0.86×1H), 6.31 (s, 0.14×1H), 3.15 (t, J=6.4 Hz, 0.86×2H), 3.04 (t, J=6.4 Hz, 0.14×2H), 2.77 (ddd, J=8.3, 5.9, 2.5 Hz, 2H), 2.37-2.31 (m, 3H), 2.05 (dp, J=44.2, 6.7 Hz, 2H); ¹³C NMR (100 MHz, CDCl₃) δ=146.4, 144.1, 137.6, 137.2, 134.3, 134.2, 133.1, 133.0, 130.7, 128.0, 127.8, 126.0, 125.8, 115.7, 115.6, 40.2, 35.7, 34.4, 33.0, 31.1, 28.4, 19.8, 19.7 ppm.

According to the characterization data, the prepared product is pure 2-(3-chloro-4-methylbenzylidene) tetrahydrothiophene (E/Z=14:86) (purity >95%); and the yield of the product is calculated to be 57%.

Example 15

Synthesis of 3-((dihydrothienyl-2(3H)-ylidene)methyl)thiophene 3-(cyclopropylethynyl)thiophene (compound corresponding to No. (15), 0.0741 g, 0.5 mmol) and sodium sulfide nonahydrate (0.2402 g, 1.0 mmol) were weighed and fed to a 25 mL reaction tube. DMA (2.5 mL) was added as a solvent, and the reaction was performed under stirring for 12 hrs at 150° C. After the reaction, the reaction solution was extracted with ethyl acetate and saturated brine, dried over anhydrous sodium sulfate and filtered with suction. The resulting filtrate was rotary evaporated to dryness, the sample was loaded, and separated by column chromatography (conditions: stationary phase 300-400-mesh silica gel powder, and mobile phase petroleum ether) to afford a reaction product (0.0620 g).

The reaction product was characterized. The results are shown below:

¹H NMR (400 MHz, CDCl₃) δ=7.23 (ddd, J=7.5, 6.9, 4.3 Hz), 7.15 (dd, J=4.9, 1.3 Hz), 7.01 (dd, J=5.0, 1.2 Hz), 6.96 (d, J=2.7 Hz), 6.50 (s, 0.88×1H), 6.42 (t, J=1.9 Hz, 0.12×1H), 3.16 (t, J=6.4 Hz, 0.88×2H), 3.04 (t, J=6.4 Hz, 0.12×2H), 2.83-2.68 (m, 2H), 2.07 (dp, J=42.7, 6.7 Hz, 2H); ¹³C NMR (100 MHz, CDCl₃) δ=144.4, 142.6, 139.6, 139.3, 128.1, 127.8, 124.9, 124.8, 120.5, 120.0, 111.7, 111.4, 39.4, 35.5, 34.5, 33.3, 31.0, 28.9 ppm.

According to the characterization data, the prepared product is pure 3-((dihydrothienyl-2(3H)-ylidene)methyl)thiophene (E/Z=12:88) (purity >95%); and the yield of the product is calculated to be 68%.

Example 16

Synthesis of (Z)-2-benzyl-3-methyltetrahydrothiophene ((1-methylcyclopropyl)ethynyl)benzene (compound corresponding to No. (16), 0.0781 g, 0.5 mmol) and sodium sulfide nonahydrate (0.2402 g, 1.0 mmol) were weighed and fed to a 25 mL reaction tube. DMA (2.5 mL) was added as a solvent, and the reaction was performed under stirring for 12 hrs at 150° C. After the reaction, the reaction solution was extracted with ethyl acetate and saturated brine, dried over anhydrous sodium sulfate and filtered with suction. The resulting filtrate was rotary evaporated to dryness, the sample was loaded, and separated by column chromatography (conditions: stationary phase 300-400-mesh silica gel powder, and mobile phase petroleum ether) to afford a reaction product (0.0343 g).

The reaction product was characterized. The results are shown below:

$^1$H NMR (400 MHz, CDCl$_3$) δ=7.51 (d, J=7.5 Hz, 2H), 7.39 (t, J=7.7 Hz, 2H), 7.20 (t, J=7.3 Hz, 1H), 6.42 (s, 1H), 3.24-3.09 (m, 2H), 2.98 (dd, J=13.3, 6.6 Hz, 1H), 2.22 (dq, J=11.9, 5.9 Hz, 1H), 1.75 (ddd, J=14.3, 12.4, 7.8 Hz, 1H), 1.32 (d, J=6.7 Hz, 3H); $^{13}$C NMR (100 MHz, CDCl$_3$) δ=147.0, 137.4, 127.8, 127.4, 125.3, 115.9, 44.5, 35.9, 31.9, 18.4 ppm.

According to the characterization data, the prepared product is pure (Z)-2-benzyl-3-methyltetrahydrothiophene (purity >95%); and the yield of the product is calculated to be 36%.

While preferred embodiments of the present invention have been described above, the present invention is not limited thereto. It should be appreciated that some improvements and variations can be made by those skilled in the art without departing from the technical principles of the present invention, which are also contemplated to be within the scope of the present invention.

What is claimed is:

1. A method for synthesizing a 2-benzylidene tetrahydrothiophene derivative, comprising the step of:

reacting a (cyclopropylethynyl) aromatic cyclic compound of Formula (I) with a sulfur source in an organic solvent as a reaction medium in air atmosphere at 100-200° C. to obtain a 2-benzylidene tetrahydrothiophene derivative of Formula (III), wherein the reaction route is as follows:

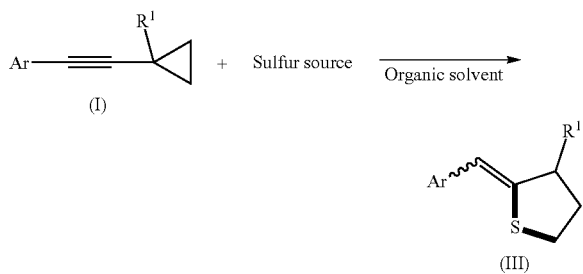

where Ar is selected from phenyl ring, a substituted phenyl ring, biphenylyl, thiophenyl ring or naphthyl ring, in which the substituent on the substituted phenyl ring is selected from the group consisting of halo, trifluoromethyl, cyano, a C$_1$-C$_{20}$ alkyl group and any combination thereof; and R$^1$ is selected from hydrogen or a C$_1$-C$_{20}$ alkyl group.

2. The method for synthesizing a 2-benzylidene tetrahydrothiophene derivative according to claim 1, wherein Ar is phenyl ring, and R$^1$ is hydrogen or methyl.

3. The method for synthesizing a 2-benzylidene tetrahydrothiophene derivative according to claim 1, wherein Ar is selected from a substituted phenyl ring, biphenylyl, thiophenyl ring or naphthyl ring, in which the substituent on the substituted phenyl ring is selected from the group consisting of halo, trifluoromethyl, cyano a C$_1$-C$_{20}$ alkyl and any combination thereof, and R$^1$ is hydrogen.

4. The method for synthesizing a 2-benzylidene tetrahydrothiophene derivative according to claim 1, wherein the (cyclopropylethynyl) aromatic cyclic compound of Formula (I) is (cyclopropylethynyl)benzene, 1-chloro-4-(cyclopropylethynyl)-benzene, 1-bromo-4-(cyclopropylethynyl)benzene, 1-(cyclopropylethynyl)-4-(tri-fluoromethyl)benzene, 1-(cyclopropylethynyl)-4-methylbenzene, 4-(cyclopropylethynyl)benzonitrile, 1-chloro-2-(cyclopropylethynyl)benzene, 1-(cyclopropyl-ethynyl)-2-methylbenzene, 1-(cyclopropylethynyl)-3-methylbenzene), 1-chloro-3-(cyclopropylethynyl)benzene, 4-(cyclopropylethynyl)-1,1'-biphenyl, 1-(cyclopropyl-ethynyl)naphthalene, 4-bromo-1-(cyclopropylethynyl)-2-methylbenzene, 2-chloro-4-(cyclopropylethynyl)-1-methylbenzene, 3-(cyclopropylethynyl)thiophene, or ((1-methylcyclopropyl)ethynyl)benzene.

5. The method for synthesizing a 2-benzylidene tetrahydrothiophene derivative according to claim 1, wherein the sulfur source is sodium sulfide and/or potassium sulfide.

6. The method for synthesizing a 2-benzylidene tetrahydrothiophene derivative according to claim 5, wherein the sulfur source is sodium sulfide nonahydrate.

7. The method for synthesizing a 2-benzylidene tetrahydrothiophene derivative according to claim 1, wherein the molar ratio of the (cyclopropylethynyl) aromatic cyclic compound to the sulfur source is 1:1-6.

8. The method for synthesizing a 2-benzylidene tetrahydrothiophene derivative according to claim 1, wherein the organic solvent is selected from the group consisting of N,N'-dimethyl formide, dimethyl sulfoxide, N,N'-dimethyl acetamide and any combination thereof.

9. The method for synthesizing a 2-benzylidene tetrahydrothiophene derivative according to claim 1, wherein in units of mole and milliliter respectively, the ratio of the (cyclopropylethynyl) aromatic cyclic compound and the organic solvent is 0.3-1 mol:0.1-10 mL.

10. The method for synthesizing a 2-benzylidene tetrahydrothiophene derivative according to claim 1, wherein the reaction time is 8-20 hrs.

11. The method for synthesizing a 2-benzylidene tetrahydrothiophene derivative according to claim 1, wherein the reaction temperature is 130-150° C.

* * * * *